United States Patent
Petkova et al.

(10) Patent No.: US 12,247,017 B2
(45) Date of Patent: Mar. 11, 2025

(54) HERBICIDAL URACILPYRIDINES

(71) Applicant: BASF SE, Ludwigshafen (DE)

(72) Inventors: Desislava Slavcheva Petkova, Ludwigshafen (DE); Matthias Witschel, Ludwigshafen (DE); Tobias Seiser, Ludwigshafen (DE); Trevor William Newton, Limburgerhof (DE); Laetitia Souillart, Wuppertal (DE)

(73) Assignee: BASF SE, Ludwigshafen (DE)

( * ) Notice: Subject to any disclaimer, the term of this patent is extended or adjusted under 35 U.S.C. 154(b) by 563 days.

(21) Appl. No.: 17/627,149

(22) PCT Filed: Jul. 21, 2020

(86) PCT No.: PCT/EP2020/070512
§ 371 (c)(1),
(2) Date: Jan. 14, 2022

(87) PCT Pub. No.: WO2021/018664
PCT Pub. Date: Feb. 4, 2021

(65) Prior Publication Data
US 2022/0274946 A1 Sep. 1, 2022

(30) Foreign Application Priority Data
Aug. 1, 2019 (EP) .................... 19189576

(51) Int. Cl.
*C07D 401/04* (2006.01)
*A01N 43/54* (2006.01)
*A01P 13/00* (2006.01)

(52) U.S. Cl.
CPC ........... *C07D 401/04* (2013.01); *A01N 43/54* (2013.01); *A01P 13/00* (2021.08)

(58) Field of Classification Search
CPC ........ C07D 401/04; A01P 13/00; A01N 43/54
See application file for complete search history.

(56) References Cited

U.S. PATENT DOCUMENTS 8,193,198 B2  6/2012  Ko et al.

FOREIGN PATENT DOCUMENTS

| EP | 2343284 | A2 | 7/2011 | |
| EP | 3028573 | A1 | 6/2016 | |
| WO | WO-99/52892 | A2 | 10/1999 | |
| WO | WO9952892 | A | * 10/1999 | |
| WO | WO-2006/125746 | A1 | 11/2006 | |
| WO | WO-2010/038953 | A2 | 4/2010 | |
| WO | WO-2013/154396 | A1 | 10/2013 | |
| WO | WO-2017/011288 | A1 | 1/2017 | |
| WO | WO-2017/202768 | A1 | 11/2017 | |
| WO | WO-2018029029 | A1 | * 2/2018 | ............. A01N 43/48 |

OTHER PUBLICATIONS

International Application No. PCT/EP2020/070512, International Search Report and Written Opinion, mailed Oct. 13, 2020.
Coleman, et al., "p-phenylazobenzoyl chloride-[benzoyl chloride, p-phenylazo-]", Organic Syntheses, Coll. vol. 3, 1955, 3 pages.
European Search Report for EP Patent Application No. 19189576.2, Issued on Jan. 24, 2020, 4 pages.
Meyers, et al., "2,2'-dimethoxy-6-formylbiphenyl-[(1,1'-biphenyl)-2-carboxaldehyde, 2',6-dimethoxy-]", Organic Syntheses, vol. 71, 1993, 7 pages.
Scheifele, et al., "2-aminobenzophenone-[benzophenone, 2-amino-]", Organic Syntheses, Coll. vol. 4, 1963, 6 pages.

* cited by examiner

*Primary Examiner* — D Margaret M Seaman
(74) *Attorney, Agent, or Firm* — MARSHALL, GERSTEIN & BORUN LLP

(57) ABSTRACT

The present invention relates to uracilpyridines of formula (I), or their agriculturally acceptable salts, wherein the variables are defined according to the description, process for preparation their use as herbicides, i.e. for controlling harmful plants, and also a method for controlling unwanted vegetation which comprises allowing a herbicidal effective amount of at least one uracil pyridine of formula (I) to act on plants, their seed and/or their habitat.

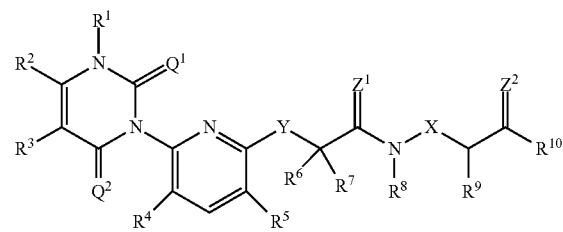

(I)

11 Claims, No Drawings

HERBICIDAL URACILPYRIDINES

CROSS-REFERENCE TO RELATED APPLICATIONS

This is the U.S. national phase of International Application No. PCT/EP2020/070512, filed Jul. 21, 2020, which claims the benefit of European Patent Application No. 19189576.2, filed on Aug. 1, 2019.

The present invention relates to uracilpyridines of formula (I) defined below and to their use as herbicides.

WO 10/38953 describes structurally similar compounds for which herbicidal action is stated, which differ from the according to the present invention that the uracil is substituted by a phenyl, whereas the uracil according to the invention is substituted by a pyridyl.

However, the herbicidal properties of these known compounds regarding the undesired vegetation are not always entirely satisfactory.

It is therefore an object of the present invention to provide uracilpyridines of formula (I) having improved herbicidal action. To be provided are in particular uracilpyridines of formula (I) which have high herbicidal activity, in particular even at low application rates, and which are sufficiently compatible with crop plants for commercial utilization.

These and further objects are achieved by uracilpyridines of formula (I), defined below, and by their agriculturally suitable salts.

Accordingly, the present invention provides uracilpyridines of formula (I)

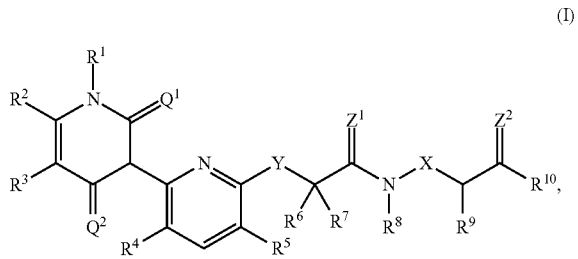

wherein the substituents have the following meanings
$R^1$ $NH_2$ or $C_1$-$C_6$-alkyl;
$R^2$ $C_1$-$C_3$-haloalkyl or $C_1$-$C_3$-alkoxy-$C_1$-haloalkyl;
$R^3$ H or $C_1$-$C_6$-alkyl;
$R^4$ H, F or Cl;
$R^5$ H, halogen or CN;
$R^6$ H or $C_1$-$C_6$-alkyl;
$R^7$ H or $C_1$-$C_6$-alkyl;
$R^8$ H, OH, $C_1$-$C_6$-alkoxy, $C_2$-$C_6$-alkenyl, $C_3$-$C_6$-alkynyl, $C_1$-$C_6$-haloalkyl or $C_1$-$C_6$-alkoxy-$C_1$-$C_6$-alkyl;
$R^9$ H, $C_1$-$C_6$-haloalkyl or $C_1$-$C_6$-alkoxycarbonyl-$C_1$-$C_6$-alkyl;
$R^{10}$ $OR^{11}$, $SR^{11}$, $NR^{12}OR^{13}$ or $NHS(O)_2R^{14}$;
  $R^{11}$ H, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, $C_1$-$C_6$-alkoxycarbonyl-$C_1$-$C_6$-alkyl, di($C_1$-$C_6$-alkyl)amino, $C_3$-$C_6$-cycloalkyl, $C_3$-$C_6$-cycloalkyl-$C_1$-$C_6$-alkyl or phenyl-$C_1$-$C_4$-alkyl;
  $R^{12}$ H, $C_1$-$C_6$-alkyl, $C_2$-$C_6$-alkenyl, $C_3$-$C_6$-alkynyl, $C_1$-$C_6$-haloalkyl or $C_1$-$C_6$-alkoxy-$C_1$-$C_6$-alkyl;
  $R^{13}$ H, $C_2$-$C_6$-alkenyl or $C_3$-$C_6$-alkynyl
  $R^{14}$ $C_1$-$C_6$-alkyl or di($C_1$-$C_6$-alkyl)amino;
$Q^1$ O or S;
$Q^2$ O or S;
X $C_1$-$C_6$-alkylene or $C_1$-$C_6$-haloalkylene;
Y O, S, S(O), $S(O)_2$, NH or N($C_1$-$C_6$-alkyl);
$Z^1$ O or S;
$Z^2$ O or S;
including their agriculturally acceptable salts, amides, esters or thioesters, provided the compounds of formula (I) have a carboxyl group.

The present invention also provides formulations comprising at least one uracilpyridine of formula (I) and auxiliaries customary for formulating crop protection agents.

The present invention also provides the use of uracilpyridines of formula (I) as herbicides, i.e. for controlling undesired vegetation.

The present invention furthermore provides a method for controlling undesired vegetation where a herbicidal effective amount of at least one uracilpyridine of formula (I) is allowed to act on plants, their seeds and/or their habitat.

Moreover, the invention relates to a process for preparing uracilpyridines of formula (I).

If the uracilpyridines of formula (I), as described herein are capable of forming geometrical isomers, for example E/Z isomers, it is possible to use both, the pure isomers and mixtures thereof, according to the invention.

If the uracilpyridines of formula (I) as described herein have one or more centres of chirality and, as a consequence, are present as enantiomers or diastereomers, it is possible to use both, the pure enantiomers and diastereomers and their mixtures, according to the invention.

If the uracilpyridines of formula (I) as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diethylammonium, diisopropylammonium, trimethylammonium, triethylammonium, tris(isopropyl)ammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Uracilpyridines of formula (I) as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

The organic moieties mentioned in the definition of the variables $R^1$ to $R^{14}$, X and Y, are—like the term halogen—collective terms for individual enumerations of the individual group members. The term halogen denotes in each case fluorine, chlorine, bromine or iodine. All hydrocarbon chains can be straight-chain or branched, the prefix $C_n$-$C_m$, denoting in each case the possible number of carbon atoms in the group.

Examples of such meanings are:

$C_1$-$C_3$-alkyl: $CH_3$, $C_2H_5$, n-propyl, and $CH(CH_3)_2$;

$C_1$-$C_4$-alkyl: for example $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkyoxy-$C_1$-$C_6$-alkyl, $C_1$-$C_6$-alkoxycarbonyl-$C_1$-$C_6$-alkyl, $C_3$-$C_6$-cycloalkyl-$C_1$-$C_6$-alkyl or phenyl $C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_3$-haloalkyl: $C_1$-$C_3$-alkyl as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl;

$C_1$-$C_4$-haloalkyl: $C_1$-$C_4$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl: $C_3$-$C_6$-alkenyl as mentioned above, and also ethenyl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_1$-$C_3$-alkoxy: methoxy, ethoxy, propoxy, 1-methylethoxy;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkoxy-$C_1$-$C_6$-alkyl, $C_1$-$C_6$-alkoxycarbonyl-$C_1$-$C_6$-alkyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di (1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl) amino, N-(1,1-dimethylethyl)-N-methylamino, N-ethyl-N-propylamino, N-ethyl-N-(1-methylethyl) amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methyl propyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methyl-propyl)amino, N-(1,1-dimethylethyl)-N-(1-methylethyl)amino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl) amino, N-methyl-N-(1-ethylpropyl)amino, N-methyl-N-hexylamino, N-methyl-N-(1,1-dimethylpropyl) amino, N-methyl-N-(1,2-dimethylpropyl)amino, N-methyl-N-(1-methylpentyl)amino, N-methyl-N-(2-methylpentyl)amino, N-methyl-N-(3-methylpentyl) amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl) amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl) amino, N-ethyl-N-(3-methylbutyl)amino, N-ethyl-N-(2,2-dimethylpropyl)amino, N-ethyl-N-(1-ethylpropyl) amino, N-ethyl-N-hexylamino, N-ethyl-N-(1,1-dimethylpropyl)amino, N-ethyl-N-(1,2-dimethylpropyl)amino, N-ethyl-N-(1-methylpentyl) amino, N-ethyl-N-(2-methyl-pentyl)amino, N-ethyl-N-(3-methylpentyl)amino, N-ethyl-N-(4-methylpentyl) amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl) amino, N-ethyl-N-(2,3-dimethylbutyl)amino, N-ethyl-N-(3,3-dimethylbutyl)amino, N-ethyl-N-(1-ethylbutyl) amino, N-ethyl-N-(2-ethylbutyl)amino, N-ethyl-N-(1, 1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclopentyl and cyclohexyl;

The preferred embodiments of the invention mentioned herein below have to be understood as being preferred either independently from each other or in combination with one another.

According to a preferred embodiment of the invention preference is also given to those uracilpyridines of formula (I), wherein the variables, either independently of one another or in combination with one another, have the following meanings:

Preferred are the uracilpyridines of formula (I), wherein $R^1$ is
 $NH_2$ or $CH_3$;
 particularly preferred $CH_3$.

Also preferred are the uracilpyridines of formula (I), wherein $R^2$ is
 $C_1$-$C_3$-haloalkyl;
 particularly preferred $C_1$-$C_2$-haloalkyl;
 especially preferred $CF_3$.

Also preferred are the uracilpyridines of formula (I), wherein $R^3$ is
 H or $CH_3$;
 particularly preferred H;
 also particularly preferred $CH_3$.

Also preferred are the uracilpyridines of formula (I), wherein $R^4$ is
 H or F;
 particularly preferred H;
 also particularly preferred F.

Also preferred are the uracilpyridines of formula (I), wherein $R^5$ is
 F, Cl, Br or CN;
 particularly preferred Cl or Br;
 especially preferred Cl.

Also preferred are the uracilpyridines of formula (I), wherein $R^6$ is
 H or $CH_3$;
 particularly preferred H;
 also particularly preferred $CH_3$.

Also preferred are the uracilpyridines of formula (I), wherein $R^7$ is
 H or $CH_3$;
 particularly preferred H.

Also preferred are the uracilpyridines of formula (I), wherein $R^8$ is
H, OH, $C_1$-$C_6$-alkyl, $C_2$-$C_6$-alkenyl, $C_3$-$C_6$-alkynyl or $C_1$-$C_6$-alkoxy-$C_1$-$C_6$-alkyl;
particularly preferred H, $CH_3$ or $CH_3OCH_2$;
especially preferred H.

Also preferred are the uracilpyridines of formula (I), wherein $R^9$ is
H or $CH_3$;
particularly preferred H;
also particularly preferred $CH_3$.

Also preferred are the uracilpyridines of formula (I), wherein $R^{19}$ is
$OR^{11}$, $NR^{12}OR^{13}$ or $NHS(O)_2R^{14}$;
particularly preferred $OR^{11}$.

Also preferred are the uracilpyridines of formula (I), wherein $R^{11}$ is
H, $C_3$-$C_6$-alkenyl, $C_3$-$C_6$-alkynyl, $C_1$-$C_8$-haloalkyl, $C_1$-$C_6$-alkoxy-$C_1$-$C_6$-alkyl;
particularly preferred is $C_1$-$C_6$-alkyl, $C_3$-$C_6$-alkenyl or $C_3$-$C_6$-alkynyl;
especially preferred $CH_3$, $CH_2CH_3$, $CH_2CH=CH_2$, $CH_2CECH$;
also particularly preferred is $C_1$-$C_6$-alkyl;
especially preferred $CH_3$.

Also preferred are the uracilpyridines of formula (I), wherein $R^{12}$ is
H or $C_1$-$C_6$-alkyl;
particularly preferred H or $CH_3$.

Also preferred are the uracilpyridines of formula (I), wherein $R^{13}$ is
$C_1$-$C_6$-alkyl;
particularly preferred $CH_3$.

Also preferred are the uracilpyridines of formula (I), wherein $R^{14}$ is
$CH_3$, $CH_2CH_3$ or $CH(CH_3)_2$.

Also preferred are the uracilpyridines of formula (I), wherein $Q^1$ is O.

Also preferred are the uracilpyridines of formula (I), wherein $Q^2$ is O.

Also preferred are the uracilpyridines of formula (I), wherein X is
$C_1$-$C_3$-alkylene;
particularly preferred $CH_2$.

Also preferred are the uracilpyridines of formula (I), wherein Y is
O, S, S(O) or $S(O)_2$;
particularly preferred is O or S;
especially preferred is O;
also especially preferred is S.

Also preferred are the uracilpyridines of formula (I), wherein $Z^1$ is O.

Also preferred are the uracilpyridines of formula (I), wherein $Z^2$ is O.

Also preferred are the uracilpyridines of formula (I), wherein
$R^1$ is $NH_2$ or $C_1$-$C_3$-alkyl;
$R^2$ is $C_1$-$C_3$-haloalkyl;
$R^3$ is H or $CH_3$;
$R^4$ is H or F;
$R^5$ is F, Cl, Br or CN;
$R^6$ is H or $CH_3$;
$R^7$ is H or $CH_3$;
$R^5$ is H, OH, $C_1$-$C_6$-alkyl, $C_2$-$C_6$-alkenyl, $C_3$-$C_6$-alkynyl or $C_1$-$C_6$-alkoxy-$C_1$-$C_6$-alkyl;
$R^9$ is H or $CH_3$;
$R^{10}$ is $OR^{11}$, $SR^{11}$, $NR^{12}OR^{13}$ or $NHS(O)_2R^{14}$; wherein
$R^{11}$ is H, $C_3$-$C_6$-alkenyl, $C_3$-$C_6$-alkynyl, $C_1$-$C_6$-haloalkyl or $C_1$-$C_6$-alkoxy-$C_1$-$C_6$-alkyl,
$R^{12}$ is H or $C_1$-$C_6$-alkyl;
$R^{13}$ is $C_1$-$C_6$-alkyl;
$R^{14}$ is $C_1$-$C_6$-alkyl or $N(C_1$-$C_6$-alkyl$)_2$;
$Q^1$ and $Q^2$ are O;
X is $C_1$-$C_3$-alkylene;
Y is O, S, S(O) or $S(O)_2$; and
$Z^1$ and $Z^2$ are O or S;
particularly preferred
$R^1$ is $NH_2$ or $CH_3$;
$R^2$ is $C_1$-$C_2$-haloalkyl;
$R^3$ is H or $CH_3$;
$R^4$ is H or F;
$R^5$ is F, Cl, Br or CN;
$R^6$ is H or $CH_3$;
$R^7$ is H or $CH_3$;
$R^5$ is H, $CH_3$ or $CH_3OCH_2$;
$R^9$ is H or $CH_3$;
$R^{10}$ is $OR^{11}$, $NR^{12}OR^{13}$ or $NHS(O)_2R^{14}$, wherein
$R^{11}$ is H, $C_3$-$C_6$-alkenyl, $C_3$-$C_6$-alkynyl, $C_1$-$C_6$-haloalkyl or $C_1$-$C_6$-alkoxy-$C_1$-$C_6$-alkyl,
$R^{12}$ is H or $CH_3$;
$R^{13}$ is $CH_3$;
$R^{14}$ is $CH_3$, $CH_2CH_3$ or $CH(CH_3)_2$;
$Q^1$ and $Q^2$ are O;
X is $C_1$-$C_3$-alkylene;
Y is O, S, S(O) or $S(O)_2$; and
$Z^1$ and $Z^2$ are O;
especially preferred
$R^1$ is $CH_3$;
$R^2$ is $CF_3$;
$R^3$ is H or $CH_3$;
$R^4$ F;
$R^5$ Cl;
$R^6$ H or $CH_3$;
$R^7$ H;
$R^8$ H;
$R^9$ H or $CH_3$;
$R^{10}$ $OR^{11}$; wherein $R^{11}$ is $CH_3$, $CH_2CH_3$, $CH_2CH=CH_2$ or $CH_2C\equiv CH$;
$Q^1$ and $Q^2$ are O;
X is $CH_2$;
Y is O, S, S(O) or $S(O)_2$; and
$Z^1$ and $Z^2$ are O.

Particular preference is given to uracilpyridines of formula (I.a) (corresponds to formula (I) wherein $R^1$ is $CH_3$, $R^2$ is $CF_3$, $R^4$ is F, $R^5$ is Cl, Rand Fe are H, $R^{10}$ is $OR^{11}$, $Q^1$ and $Q^2$ are O, X is $CH_2$, Y is O, and $Z^1$ and $Z^2$ are O):

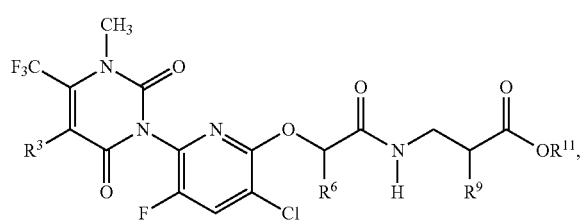

(I.a)

wherein the variables $R^3$, $R^6$, $R^9$, $R^{11}$ and Y have the meanings, in particular the preferred meanings, as defined above.

Special preference is given to the compounds of the formulae (I.a.1) to (I.a.32) of Table A, where the definitions of the variables $R^3$, $R^6$, $R^9$, $R^{11}$ and Y are of particular importance for the compounds according to the invention not only in combination with one another but in each case also on their own:

TABLE A

| No. | $R^3$ | $R^6$ | $R^9$ | $R^{11}$ |
|---|---|---|---|---|
| I.a.1. | H | H | H | $CH_3$ |
| I.a.2. | H | H | H | $CH_2CH_3$ |
| I.a.3. | H | H | H | $CH_2CH=CH_2$ |
| I.a.4. | H | H | H | $CH_2C\equiv CH$ |
| I.a.5. | H | H | $CH_3$ | $CH_3$ |
| I.a.6. | H | H | $CH_3$ | $CH_2CH_3$ |
| I.a.7. | H | H | $CH_3$ | $CH_2CH=CH_2$ |
| I.a.8. | H | H | $CH_3$ | $CH_2C\equiv CH$ |
| I.a.9. | H | $CH_3$ | H | $CH_3$ |
| I.a.10. | H | $CH_3$ | H | $CH_2CH_3$ |
| I.a.11. | H | $CH_3$ | H | $CH_2CH=CH_2$ |
| I.a.12. | H | $CH_3$ | H | $CH_2C\equiv CH$ |
| I.a.13. | $CH_3$ | H | H | $CH_3$ |
| I.a.14. | $CH_3$ | H | H | $CH_2CH_3$ |
| I.a.15. | $CH_3$ | H | H | $CH_2CH=CH_2$ |
| I.a.16. | $CH_3$ | H | H | $CH_2C\equiv CH$ |
| I.a.17. | H | $CH_3$ | $CH_3$ | $CH_3$ |
| I.a.18. | H | $CH_3$ | $CH_3$ | $CH_2CH_3$ |
| I.a.19. | H | $CH_3$ | $CH_3$ | $CH_2CH=CH_2$ |
| I.a.20. | H | $CH_3$ | $CH_3$ | $CH_2C\equiv CH$ |
| I.a.21. | $CH_3$ | H | $CH_3$ | $CH_3$ |
| I.a.22. | $CH_3$ | H | $CH_3$ | $CH_2CH_3$ |
| I.a.23. | $CH_3$ | H | $CH_3$ | $CH_2CH=CH_2$ |
| I.a.24. | $CH_3$ | H | $CH_3$ | $CH_2C\equiv CH$ |
| I.a.25. | $CH_3$ | $CH_3$ | H | $CH_3$ |
| I.a.26. | $CH_3$ | $CH_3$ | H | $CH_2CH_3$ |
| I.a.27. | $CH_3$ | $CH_3$ | H | $CH_2CH=CH_2$ |
| I.a.28. | $CH_3$ | $CH_3$ | H | $CH_2C\equiv CH$ |
| I.a.29. | $CH_3$ | $CH_3$ | $CH_3$ | $CH_3$ |
| I.a.30. | $CH_3$ | $CH_3$ | $CH_3$ | $CH_2CH_3$ |
| I.a.31. | $CH_3$ | $CH_3$ | $CH_3$ | $CH_2CH=CH_2$ |
| I.a.32. | $CH_3$ | $CH_3$ | $CH_3$ | $CH_2C\equiv CH$ |

Also preferred are the uracilpyridines of formula (I.b), particularly preferred the uracilpyridines of formulae (I.b.1) to (I.b.32), which differ from the corresponding uracilpyridines of formulae (I.a.1) to (I.a.32.) only in that Y is S:

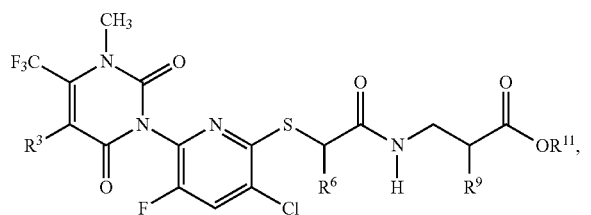
(I.b)

Also preferred are the uracilpyridines of formula (I.c), particularly preferred the uracilpyridines of formulae (I.c.1) to (I.c.32), which differ from the corresponding uracilpyridines of formulae (I.a.1) to (I.a.32.) only in that Y is S(O):

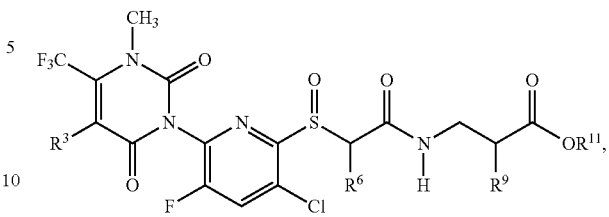
(I.c)

Also preferred are the uracilpyridines of formula (I.d), particularly preferred the uracilpyridines of formulae (I.d.1) to (I.d.32), which differ from the corresponding uracilpyridines of formulae (I.a.1) to (I.a.32.) only in that Y is $S(O)_2$:

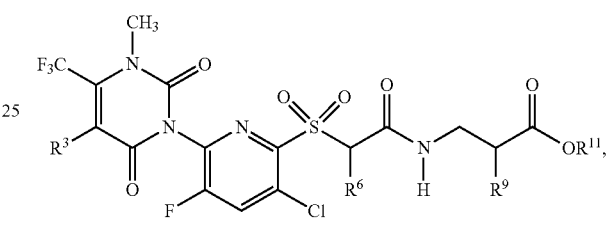
(I.d)

In a particularly preferred embodiment, the compound of formula (I) is the uracilpyridine (I.b.9):

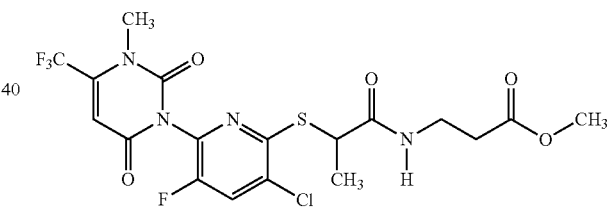
(I.b.9)

The uracilpyridines of formula (I) according to the invention can be prepared by standard processes of organic chemistry, for example by the following process A:

Process A)

The uracilpyridines of formula (I) can be obtained by reaction of acid halides of formula (II) with compounds of formula (III) in the presence of a base:

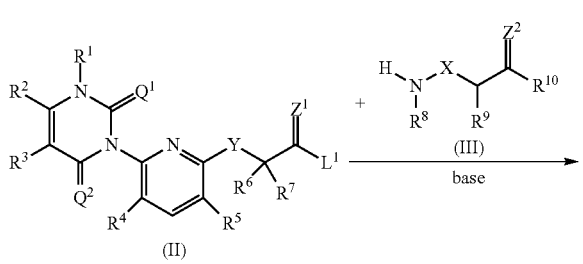

-continued

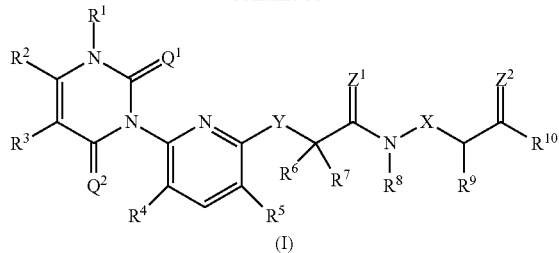

(I)

Within the acid halides of formula (II), L is a nucleophilically displaceable leaving group such as halogen; preferably is F, Cl or Br; especially preferred is F or Cl, more preferred is Cl.

Such nucleophilic substitution can be conducted in analogy to known processes (e.g. WO 10/038953 (U.S. Pat. No. 8,193,198); WO 06/125746).

Instead of the acid halides of formula (II), also the corresponding acid (e.g. acid halide of formula (II), wherein $L^1$ is OH) in combination with an activating reagent, like carbonyldiimidazole, N,N'-Dicyclohexylcarbodiimide (DCC), 1-ethyl-3-(3-dimethylaminopropyl)-carbodiimide (EDC), 1-[bis(Dimethylamin)methylen]-1H-1,2,3-triazol[4,5-b]pyridinium-3-oxid-hexafluorophosphat (HATU) or N-methyl-2-chloropyridinium chloride can be used. The reaction conditions are the same as described for the acid halides of formula (II).

The reaction of acid halides (II) with compounds (111) is usually carried out from 0° C. to the boiling point of the reaction mixture, preferably at from 0° C. to 100° C., particularly preferably at from 0° C. to 40° C., in an inert organic solvent in the presence of a base.

The reaction may in principle be carried out in substance. However, preference is given to reacting the acid halides (II) with the compounds (111) in an organic solvent. Suitable in principle are all solvents, which are capable of dissolving the acid halides (II) and the compounds (111) at least partly, and preferably fully under reaction conditions.

Examples of suitable solvents are aliphatic hydrocarbons such as pentane, hexane, cyclohexane, nitromethane and mixtures of $C_5$-$C_8$-alkanes; aromatic hydrocarbons such as benzene, chlorobenzene, toluene, cresols, o-, m- and p-xylene; halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); esters such as ethyl acetate and butyl acetate; nitriles such as acetonitrile and propionitrile; ketones such as acetone, methyl ethyl ketone, diethyl ketone, tert-butyl methyl ketone, cyclohexanone; dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers and dipolar aprotic solvents as mentioned above.

It is also possible to use mixtures of the solvents mentioned.

Examples of suitable bases include metal-containing bases and nitrogen-containing bases.

Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride; alkali metal and alkaline earth metal carbonates such as lithium carbonate, sodium carbonate, potassium carbonate, magnesium carbonate, and calcium carbonate; alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; and furthermore organic bases, such as tertiary amines such as trimethylamine, triethylamine, diisopropylethylamine, tributylamine and N-methylpiperidine, pyridine, substituted pyridines such as collidine, lutidine, N-methylmorpholine and 4-dimethylaminopyridine and also bicyclic amines.

Examples of suitable nitrogen-containing bases are $C_1$-$C_6$-alkylamines, preferably trialkylamines, for example triethylamine, trimethylamine, N-ethyldiisopropylamine; pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal carbonates and nitrogen-containing bases as defined above; especially preferred triethylamine, pyridine or sodium carbonate.

The term base as used herein also includes mixtures of two or more, preferably two of the above compounds. Particular preference is given to the use of one base.

The bases are generally used in excess, more preferably with from 1 to 3 equivalents based on the acid halides (II), and they may also be used as the solvent.

For the reaction, the acid halides (II), the compounds (111) and the base can be brought into contact in any way per se.

Accordingly, the reaction partners and the base may be introduced into the reaction vessel and reacted separately, simultaneously or successively.

The reactants are generally employed in equimolar amounts. It might be advantageous using one of the reactants in excess, for example with a view to complete a reaction of the other reactant.

The reaction can be carried out at atmospheric pressure, reduced pressure or under elevated pressure, if appropriate under an inert gas, continuously or batchwise.

The end of the reaction can easily be determined by the skilled worker by means of routine methods.

The reaction mixtures are worked up in a customary manner, for example by mixing with water, separation of the phases and, if appropriate, chromatographic purification of the crude product. Some of the intermediates and end products are obtained in the form of viscous oils, which can be purified or freed from volatile components under reduced pressure and at moderately elevated temperature.

If the intermediates and the end products are obtained as solid, purification can also be carried out by recrystallisation or digestion.

Acid halides of formula (II) (necessary for process A mentioned above) can be prepared from uracilpyridines of formula (IV):

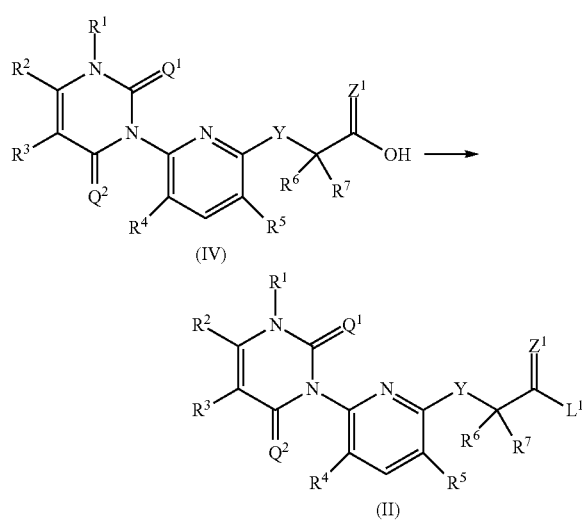

Within the acid halides of formula (II), L is halogen; preferably is F, Cl or Br; especially preferred is F or Cl, more preferred is Cl.

Suitable halogenating agents are e.g. $POCl_3$, $POBr_3$, $PCl_3$, $PBr_3$, $PCl_5$, $PBr_5$, $SOCl_2$, $SOBr_2$, oxalyl chloride, phosgene, diphosgene, triphosgene, cyanuric chloride, cyanuric fluoride and diethylaminosulfur trifluoride (DAST).

According to a preferred embodiment of the present invention, a chlorinating agent is used as the halogenating agent. Preferably, $POCl_3$, $SOCl_2$, oxalyl chloride, phosgene, diphosgene, triphosgene are used as the chlorinating agent.

For example, acid chlorides can be prepared by chlorinating uracilpyridines of formula (IV). Suitable chlorinating agents are, for example, thionyl chloride, oxalyl chloride, phosphorus trichloride, phosphorus pentachloride, phosphorus oxychloride, phosgene, diphosgene or triphosgene.

More information for carrying out such chlorination reactions are disclosed in the following references: A. J. Meyers and M. E. Flanagan, Org. Synth. 71, 107 (1992); H. J. Scheifele Jr. and D. F. DeTar, Org. Synth. Coll. Vol. IV, page 34 (1963); G. H. Coleman et al., Org. Synth. Coll. Vol. III, page 712 (1955); H. Henecka in Houben-Weyl, Methoden der Organischen Chemie [Methods in Organic Chemistry], Vol. VIII, 4th Edition, Stuttgart 1952, page 463 et seq.

The compounds of formula (III) are commercially available or known from literature.

The uracilpyridines of formula (IV) can be prepared in analogy to WO 99/52892.

To widen the spectrum of action and to achieve synergistic effects, the uracilpyridines of formula (I) may be combined with many representatives of other herbicidal or growth-regulating active ingredient groups and then applied concomitantly. Suitable components for combinations are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamides, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

It may furthermore be beneficial to apply the uracilpyridines of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

The invention also relates to formulations comprising at least an auxiliary and at least one uracilpyridine of formula (I) according to the invention.

A formulation comprises a pesticidally effective amount of a uracilpyridine of formula (I). The term "effective amount" denotes an amount of the uracilpyridines of formula (I), which is sufficient for controlling undesired vegetation, especially for controlling undesired vegetation in crops (i.e. cultivated plants) and which does not result in a substantial damage to the treated crop plants. Such an amount can vary in a broad range and is dependent on various factors, such as the undesired vegetation to be controlled, the treated crop plants or material, the climatic conditions and the specific uracilpyridine of formula (I) used.

The uracilpyridines of formula (I), their N-oxides, salts, amides, esters or thioesters can be converted into customary types of formulations, e. g. solutions, emulsions, suspensions, dusts, powders, pastes, granules, pressings, capsules, and mixtures thereof. Examples for formulation types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further formulation types are defined in the "Catalogue of pesticide formulation types and international coding system", Technical Monograph No. 2, 6$^{th}$ Ed. May 2008, CropLife International.

The formulations are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetting agents, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates;

amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the uracilpyridines of formula (I) on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for formulation types and their preparation are:
i) Water-Soluble Concentrates (SL, LS)

10-60 wt % of an uracilpyridine of formula (I) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of an uracilpyridine of formula (I) according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of an uracilpyridine of formula (I) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of an uracilpyridine of formula (I) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of an uracilpyridine of formula (I) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type formulation up to 40 wt % binder (e.g. polyvinylalcohol) is added.

vi) Water-Dispersible Granules and Water-Soluble Granules (WG, SG)

50-80 wt % of an uracilpyridine of formula (I) according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of an uracilpyridine of formula (I) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of an uracilpyridine of formula (I) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of an uracilpyridine of formula (I) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of an uracilpyridine of formula (I) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of an uracilpyridine of formula (I) according to the invention, 0-40 wt % water insoluble organic solvent (e.g. aromatic hydrocarbon), and an isocyanate monomer (e.g. diphenylmethane-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS formulation.

ix) Dustable Powders (DP, DS)

1-10 wt % of an uracilpyridine of formula (I) according to the invention are ground finely and mixed intimately with solid carrier (e.g. finely divided kaolin) ad 100 wt %.

x) Granules (GR, FG)

0.5-30 wt % of an uracilpyridine of formula (I) according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of an uracilpyridine of formula (I) according to the invention are dissolved in organic solvent (e.g. aromatic hydrocarbon) ad 100 wt %.

The formulation types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The formulations generally comprise between 0.01 and 95%, preferably between 0.1 and 90%, and in particular between 0.5 and 75%, by weight of the uracilpyridines of formula (I).

The uracilpyridines of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The formulations in question give, after two-to-tenfold dilution, active substance concentrations of from 0.01 to 60% by weight, preferably from 0.1 to 40% by weight, in the ready-to-use preparations.

Methods for applying uracilpyridines of formula (I) or formulations thereof, on to plant propagation material, especially seeds, include dressing, coating, pelleting, dusting, soaking and in-furrow application methods of the propagation material. Preferably, uracilpyridines of formula (I) or formulations thereof, are applied on to the plant propagation material by a method such that germination is not induced, e. g. by seed dressing, pelleting, coating and dusting.

Various types of oils, wetting agents, adjuvants, fertilizer, or micronutrients, and further pesticides (e.g. herbicides, insecticides, fungicides, growth regulators, safeners) may be added to the uracilpyridines of formula (I) or the formulations comprising them as premix or, if appropriate not until immediately prior to use (tank mix). These agents can be admixed with the formulations according to the invention in a weight ratio of 1:100 to 100:1, preferably 1:10 to 10:1.

The user applies the uracilpyridines of formula (I) according to the invention or the formulations comprising them usually from a pre-dosage device, a knapsack sprayer, a spray tank, a spray plane, or an irrigation system. Usually, the formulation is made up with water, buffer, and/or further auxiliaries to the desired application concentration and the ready-to-use spray liquor or the formulation according to the invention is thus obtained. Usually, 20 to 2000 liters, preferably 50 to 400 liters, of the ready-to-use spray liquor are applied per hectare of agricultural useful area.

According to one embodiment, either individual components of the formulation according to the invention or partially premixed components, e. g. components comprising uracilpyridines of formula (I), may be mixed by the user in a spray tank and further auxiliaries and additives may be added, if appropriate.

In a further embodiment, individual components of the formulation according to the invention such as parts of a kit or parts of a binary or ternary combination may be mixed by the user himself in a spray tank and further auxiliaries may be added, if appropriate.

In a further embodiment, either individual components of the formulation according to the invention or partially premixed components, e. g components comprising uracilpyridines of formula (I) can be applied jointly (e.g. after tank mix) or consecutively.

The uracilpyridines of formula (I), are suitable as herbicides. They are suitable as such or as an appropriate formulation.

The uracilpyridines of formula (I) or the formulations comprising them, control undesired vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

The uracilpyridines of formula (I) or the formulations comprising them, are applied to the plants mainly by spraying the leaves. Here, the application can be carried out using, for example, water as carrier by customary spraying techniques using spray liquor amounts of from about 100 to 1000 l/ha (for example from 300 to 400 l/ha). The uracilpyridines of formula (I) or the formulations comprising them, may also be applied by the low-volume or the ultra-low-volume method, or in the form of microgranules.

Application of the uracilpyridines of formula (I) or the formulations comprising them, can be done before, during and/or after, preferably during and/or after, the emergence of the undesired vegetation.

Application of the uracilpyridines of formula (I) or the formulations comprising them can be carried out before or during sowing.

The uracilpyridines of formula (I) or the formulations comprising them, can be applied pre-, post-emergence or pre-plant, or together with the seed of a crop plant. It is also possible to apply the uracilpyridines of formula (I) or the formulations comprising them, by applying seed, pretreated with the uracilpyridines of formula (I) or the formulations comprising them, of a crop plant. If the active ingredients are less well tolerated by certain crop plants, application techniques may be used in which the uracilpyridines of formula (I) or the formulations comprising them are sprayed, with the aid of the spraying equipment, in such a way that as far as possible they do not come into contact with the leaves of the sensitive crop plants, while the active ingredients reach the leaves of undesired vegetation growing underneath, or the bare soil surface (post-directed, layby).

In a further embodiment, the uracilpyridines of formula (I) or the formulations comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the uracilpyridines of formula (I) or the formulations prepared therefrom. Here, the combinations can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the crop plants mentioned above, but also the seed of transgenic plants or plants obtained by customary breeding methods.

When employed in plant protection, the amounts of active substances applied, i.e. the uracilpyridines of formula (I) without formulation auxiliaries, are, depending on the kind of effect desired, from 1 to 2000 g per ha, preferably from 3 to 1600 g per ha, more preferably from 6 to 800 g per ha and in particular from 10 to 400 g per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. the uracilpyridines of formula (I) are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Depending on the application method in question, the uracilpyridines of formula (I) or the formulations comprising them, can additionally be employed in a further number of crop plants for eliminating undesired vegetation. Examples of suitable crops are the following: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec.*, Manihot esculenta, Medicago sativa, Musa* spec.*, Nicotiana tabacum (N. rustica), Olea europaea, Oryza sativa, Phaseolus lunatus, Phaseolus vulgaris, Picea abies, Pinus* spec.*, Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor (S. vulgare), Theobroma cacao, Trifolium pratense, Triticum aestivum, Triticale, Triticum durum, Vicia faba, Vitis vinifera* and *Zea mays*.

Preferred crops are *Arachis hypogaea, Beta vulgaris* spec. *altissima, Brassica napus* var. *napus, Brassica oleracea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus* spec.*, Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (S. vulgare), Triticale, Triticum aestivum, Triticum durum, Vicia faba, Vitis vinifera* and *Zea mays*.

Especially preferred crops are crops of cereals, corn, soybeans, rice, oilseed rape, cotton, sunflower or permanent crops.

The uracilpyridines of formula (I) according to the invention or the formulations comprising them, can also be used in crops which have been modified by mutagenesis or genetic engineering in order to provide a new trait to a plant or to modify an already present trait.

The term "crops" as used herein includes also (crop) plants which have been modified by mutagenesis or genetic engineering in order to provide a new trait to a plant or to modify an already present trait.

Mutagenesis includes techniques of random mutagenesis using X-rays or mutagenic chemicals, but also techniques of targeted mutagenesis, in order to create mutations at a specific locus of a plant genome. Targeted mutagenesis techniques frequently use oligonucleotides or proteins like CRISPR/Cas, zinc-finger nucleases, TALENs or meganucleases to achieve the targeting effect.

Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant in order to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name. Traits which have been introduced in plants or have been modified include in particular herbicide tolerance, insect resistance, increased yield and tolerance to abiotic conditions, like drought.

Herbicide tolerance has been created by using mutagenesis as well as using genetic engineering. Plants which have been rendered tolerant to acetolactate synthase (ALS) inhibitor herbicides by conventional methods of mutagenesis and breeding comprise plant varieties commercially available under the name Clearfield®. However, most of the herbicide tolerance traits have been created via the use of transgenes.

Herbicide tolerance has been created to glyphosate, glufosinate, 2,4-D, dicamba, oxynil herbicides, like bromoxynil and ioxynil, sulfonylurea herbicides, ALS inhibitor herbicides and 4-hydroxyphenyl pyruvate dioxygenase (HPPD) inhibitors, like isoxaflutole and mesotrione.

Transgenes which have been used to provide herbicide tolerance traits comprise: for tolerance to glyphosate: cp4 epsps, epsps grg23ace5, mepsps, 2mepsps, gat4601, gat4621 and goxv247, for tolerance to glufosinate: pat and bar, for tolerance to 2,4-D: aad-1 and aad-12, for tolerance to dicamba: dmo, for tolerance to oxynil herbicides: bxn, for tolerance to sulfonylurea herbicides: zm-hra, csr1-2, gm-hra, S4-HrA, for tolerance to ALS inhibitor herbicides: csr1-2, for tolerance to HPPD inhibitor herbicides: hppdPF, W336 and avhppd-03.

Transgenic corn events comprising herbicide tolerance genes are for example, but not excluding others, DAS40278, MON801, MON802, MON809, MON810, MON832, MON87411, MON87419, MON87427, MON88017, MON89034, NK603, GA21, MZHG0JG, HCEM485, VCO-Ø1981-5, 676, 678, 680, 33121, 4114, 59122, 98140, Bt10, Bt176, CBH-351, DBT418, DLL25, MS3, MS6, MZIR098, T25, TC1507 and TC6275.

Transgenic soybean events comprising herbicide tolerance genes are for example, but not excluding others, GTS 40-3-2, MON87705, MON87708, MON87712, MON87769, MON89788, A2704-12, A2704-21, A5547-127, A5547-35, DP356043, DAS44406-6, DAS68416-4, DAS-81419-2, GU262, SYHTØH2, W62, W98, FG72 and CV127.

Transgenic cotton events comprising herbicide tolerance genes are for example, but not excluding others, 19-51a, 31707, 42317, 81910, 281-24-236, 3006-210-23, BXN10211, BXN10215, BXN10222, BXN10224, MON1445, MON1698, MON88701, MON88913, GHB119, GHB614, LLCotton25, T303-3 and T304-40.

Transgenic canola events comprising herbicide tolerance genes are for example, but not excluding others, MON88302, HCR-1, HCN10, HCN28, HCN92, MS1, MS8, PHY14, PHY23, PHY35, PHY36, RF1, RF2 and RF3.

Insect resistance has mainly been created by transferring bacterial genes for insecticidal proteins to plants. Transgenes which have most frequently been used are toxin genes of Bacillus spec. and synthetic variants thereof, like cry1A, cry1Ab, cry1Ab-Ac, cry1Ac, cry1A.105, cry1F, cry1Fa2, cry2Ab2, cry2Ae, mcry3A, ecry3.1Ab, cry3Bb1, cry34Ab1, cry35Ab1, cry9C, vip3A(a), vip3Aa20. However, also genes of plant origin have been transferred to other plants. In particular genes coding for protease inhibitors, like CpTI and pinII. A further approach uses transgenes in order to produce double stranded RNA in plants to target and downregulate insect genes. An example for such a transgene is dvsnf7.

Transgenic corn events comprising genes for insecticidal proteins or double stranded RNA are for example, but not excluding others, Bt10, Bt11, Bt176, MON801, MON802, MON809, MON810, MON863, MON87411, MON88017, MON89034, 33121, 4114, 5307, 59122, TC1507, TC6275, CBH-351, MIR162, DBT418 and MZIR098.

Transgenic soybean events comprising genes for insecticidal proteins are for example, but not excluding others, MON87701, MON87751 and DAS-81419.

Transgenic cotton events comprising genes for insecticidal proteins are for example, but not excluding others, SGK321, MON531, MON757, MON1076, MON15985, 31707, 31803, 31807, 31808, 42317, BNLA-601, Event1, COT67B, COT102, T303-3, T304-40, GFM Cry1A, GK12, MLS 9124, 281-24-236, 3006-210-23, GHB119 and SGK321.

Increased yield has been created by increasing ear biomass using the transgene athb17, being present in corn event MON87403, or by enhancing photosynthesis using the transgene bbx32, being present in the soybean event MON87712.

Crops comprising a modified oil content have been created by using the transgenes: gm-fad2-1, Pj.D6D, Nc.Fad3, fad2-1A and fatb1-A. Soybean events comprising at least one of these genes are: 260-05, MON87705 and MON87769.

Tolerance to abiotic conditions, in particular to tolerance to drought, has been created by using the transgene cspB, comprised by the corn event MON87460 and by using the transgene Hahb-4, comprised by soybean event IND-ØØ41Ø-5.

Traits are frequently combined by combining genes in a transformation event or by combining different events during the breeding process. Preferred combination of traits are herbicide tolerance to different groups of herbicides, insect tolerance to different kind of insects, in particular tolerance to lepidopteran and coleopteran insects, herbicide tolerance with one or several types of insect resistance, herbicide tolerance with increased yield as well as a combination of herbicide tolerance and tolerance to abiotic conditions.

Plants comprising singular or stacked traits as well as the genes and events providing these traits are well known in the art. For example, detailed information as to the mutagenized or integrated genes and the respective events are available from websites of the organizations "International Service for the Acquisition of Agri-biotech Applications (ISAAA)" (http://www.isaaa.org/gmapprovaldatabase) and the "Center for Environmental Risk Assessment (CERA)" (http://cera-qmc.orq/GMCropDatabase), as well as in patent applications, like EP3028573 and WO2017/011288.

The use of the compounds of formula (I) or formulations or combinations comprising them according to the invention on crops may result in effects which are specific to a crop comprising a certain gene or event. These effects might involve changes in growth behavior or changed resistance to biotic or abiotic stress factors. Such effects may in particular comprise enhanced yield, enhanced resistance or tolerance to insects, nematodes, fungal, bacterial, mycoplasma, viral or viroid pathogens as well as early vigour, early or delayed ripening, cold or heat tolerance as well as changed amino acid or fatty acid spectrum or content.

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the uracilpyridines of formula (I) according to the invention, or the formulations comprising them, are also suitable for the defoliation and/or desiccation of plant parts of crops such as cotton, potato, oilseed rape, sunflower, soybean or field beans, in particular cotton. In this regard, formulations for the desiccation and/or defoliation of crop plants, processes for preparing these formulations and methods for desiccating and/or defoliating plants using the uracilpyridines of formula (I) have been found.

As desiccants, the uracilpyridines of formula (I) are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

A PREPARATION EXAMPLES

Example 1

Methyl 3-[2-[[3-chloro-5-fluoro-6-[3-methyl-2,6-dioxo-4-(trifluoromethyl)pyrimidin-1-yl]-2-pyridyl]sulfanyl]propanoylamino]propanoate [uracilpyridine (I.b.9)]

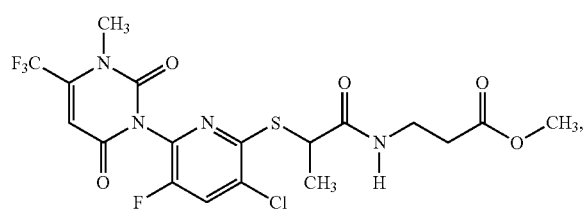 [SMILES: COC(=O)CCNC(=O)C(C)Sc1nc(-n2c(=O)cc(C(F)(F)F)n(C)c2=O)c(F)cc1Cl]

Example 1 Step 1

3-(5-chloro-3,6-difluoro-2-pyridyl)-1-methyl-6-(trifluoromethyl)pyrimidine-2,4-dione (Compound 1.1)

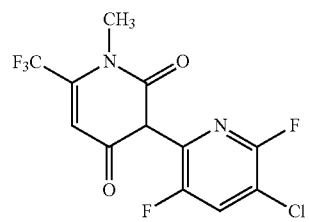 [SMILES: CN1C(=O)C(c2nc(F)c(Cl)cc2F)C(=O)C=C1C(F)(F)F]

The desired compound can be prepared in analogy to WO 2017/202768, example 5.4.

Example 1 Step 2

Ethyl 2-[[3-chloro-5-fluoro-6-[3-methyl-2,6-dioxo-4-(trifluoromethyl)pyrimidin-1-yl]-2-pyridyl]-sulfanyl]propanoate (Compound 1.2)

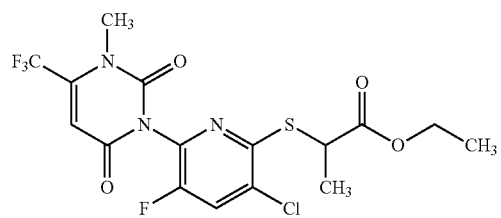 [SMILES: CCOC(=O)C(C)Sc1nc(-n2c(=O)cc(C(F)(F)F)n(C)c2=O)c(F)cc1Cl]

To a solution of 3.0 g (17 mmol) ethyl 2-acetylsulfanylpropanoate (CAS 129975-20-8) in 30 mL $CH_3CN$ was added 30 mL $CH_3OH$ and 1.2 g (8.7 mmol) $K_2CO_3$ and the solution was stirred at room temperature for 0.5 hour. Then 3.0 g (8.8 mmol) of compound 1.1 was added and the reaction mixture was stirred at room temperature for 4 days. Then water was added, the mixture was extracted with ethyl acetate, the combined organic layer was washed with water and brine, dried over anhydrous $Na_2SO_4$, filtered and the solvent was removed under reduced pressure. The crude product was purified by column chromatography on silica (petrol ether/ethyl acetate) to give 1.5 g (3.3 mmol, 19%) of the desired compound.

Example 1 Step 3

2-[[3-chloro-5-fluoro-6-[3-methyl-2,6-dioxo-4-(trifluoromethyl)pyrimidin-1-yl]-2-pyridyl]sulfanyl]-propanoic Acid (Compound 1.3)

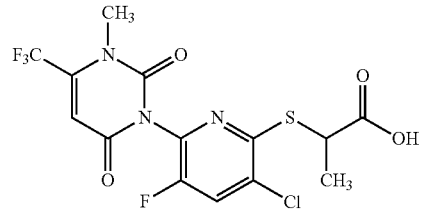 [SMILES: CC(Sc1nc(-n2c(=O)cc(C(F)(F)F)n(C)c2=O)c(F)cc1Cl)C(=O)O]

To a solution of 0.9 g (2 mmol) compound 1.2 in 10 mL dioxane was added 10 mL 3N aqueous HCl at room temperature and the mixture was stirred for 16 hours at 60° C. Then the mixture was poured into water and was extracted with ethyl acetate. The combined organic layer was washed with brine, dried over anhydrous $Na_2SO_4$, filtered and the solvent was removed under reduced pressure. The crude product was purified by column chromatography on silica (petrol ether/ethyl acetate) to give 0.4 g (0.9 mmol, 32%) of the desired compound.

$^1$H-NMR (CDCl$_3$, ppm): 7.65 (dd, J=7.7 Hz, J=3.9 Hz, 1H); 6.37 (d, J=3.1 Hz, 1H); 4.37-4.28 (m, 1H); 3.57 (br d, J=4.1 Hz, 3H); 1.64 (d, J=7.4 Hz, 3H).

Example 1 Step 4

Methyl 3-[2-[[3-chloro-5-fluoro-6-[3-methyl-2,6-dioxo-4-(trifluoromethyl)pyrimidin-1-yl]-2-pyridyl]-sulfanyl]propanoylamino]propanoate [uracilpyridine (I.b.9)]

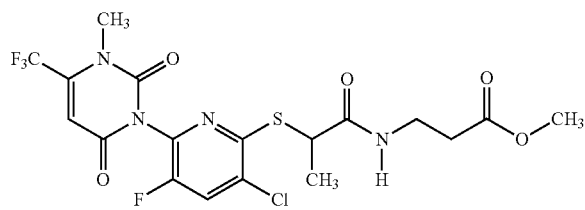 [SMILES: COC(=O)CCNC(=O)C(C)Sc1nc(-n2c(=O)cc(C(F)(F)F)n(C)c2=O)c(F)cc1Cl]

To a solution of 0.3 g (0.7 mmol) compound 1.3 in 3 mL CH$_3$CN was added 0.145 g (1.05 mmol) methyl 3-amino-propionate hydrochloride (CAS 3196-73-4), 0.53 g (1.4 mmol) 1-[bis(Dimethylamin)methylen]-1H-1,2,3-triazol[4,5-b]pyridinium-3-oxide-hexafluorophosphate (HATU, CAS 148893-10-1) and 0.45 g (3.5 mmol) N-ethyldiisopropylamine. The mixture was stirred at room temperature for 16 h and then poured into water. The mixture was extracted with ethyl acetate, the combined organic layer was washed with brine, dried over anhydrous $Na_2SO_4$, filtered and the solvent was removed under reduced pressure. The crude product was purified by preparative HPLC (acetonitrile/water containing trifluoroacetic acid) to give 0.11 g (0.2 mmol, 31%) of the desired title compound.

$^1$H-NMR (CDCl$_3$, ppm): 7.64 (d, J=7.89 Hz, 1H); 6.40 (d, J=2.63 Hz, 1H); 4.34 (dd, J=7.45 Hz, J=3.95 Hz, 1H); 3.56-3.63 (m, 6H); 3.43-3.55 (m, 1H); 3.22-3.40 (m, 1H); 2.40-2.60 (m, 2H); 1.56 (dd, J=7.45 Hz, J=1.32 Hz, 4H). [M+H]=513.0; Rt=1.096 min The compounds listed below can be prepared similarly to the example mentioned above.

Example 2 [Uracilpyridine (I.a.2)]

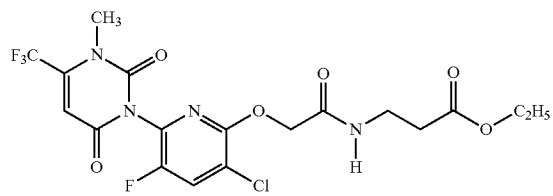 [SMILES: CCOC(=O)CCNC(=O)COc1nc(-n2c(=O)cc(C(F)(F)F)n(C)c2=O)c(F)cc1Cl]

[M+H]=497; Rt=1.046 min

B USE EXAMPLES

The herbicidal activity of the uracilpyridines of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the test plants had rooted. This cover caused uniform germination of the test plants, unless this had been impaired by the active ingredients. For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the test plants were kept at 10-25° C. or 20-35° C., respectively. The test period extended over 2 to 4 weeks. During this time, the test plants were tended, and their response to the individual treatments was evaluated.

Evaluation was carried out using a scale from 0 to 100. 100 means no emergence of the test plants, or complete destruction of at least the aerial moieties, and 0 means no damage, or normal course of growth. A good herbicidal activity is given at values of at least 70 and a very good herbicidal activity is given at values of at least 85.

The test plants used in the greenhouse experiments were of the following species:

| Bayer code | Scientific name |
|---|---|
| AMARE | *Amaranthus retroflexus* |
| CHEAL | *Chenopodium album* |
| ECHCG | *Echinocloa crus-galli* |
| SETVI | *Setaria viridis* |

At an application rate of 16 g/ha, the compound 1 [example 1; uracilpyridine (I.b.9)] applied by the post-emergence method, showed very good herbicidal activity against AMARE, CHEAL, ECHCG and SETVI.

At an application rate of 16 g/ha, example 2 [uracilpyridine (I.a.2)] applied by the post-emergence method, showed very good herbicidal activity against AMARE, CHEAL and SETVI.

The invention claimed is:

1. A uracilpyridine of formula (I)

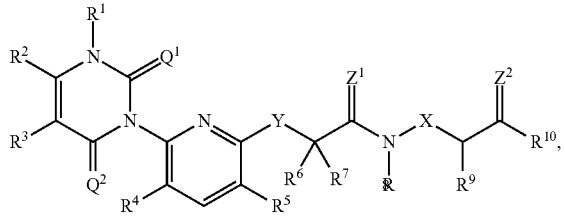

(I)

wherein the substituents have the following meanings:
$R^1$ $NH_2$ or $C_1$-$C_6$-alkyl;
$R^2$ $C_1$-$C_3$-haloalkyl or $C_1$-$C_3$-alkoxy-$C_1$-haloalkyl;
$R^3$ H or $C_1$-$C_6$-alkyl;
$R^4$ H, F or Cl;
$R^5$ H, halogen or CN;
$R^6$ H or $C_1$-$C_6$-alkyl;
$R^7$ H or $C_1$-$C_6$-alkyl;
$R^8$ H, OH, $C_1$-$C_6$-alkoxy, $C_1$-$C_6$-alkyl, $C_2$-$C_6$-alkenyl, $C_3$-$C_6$-alkynyl, $C_1$-$C_6$-haloalkyl or $C_1$-$C_6$-alkoxy-$C_1$-$C_6$-alkyl;
$R^9$ H, $C_1$-$C_6$-alkyl, $C_1$-$C_6$-haloalkyl or $C_1$-$C_6$-alkoxycarbonyl-$C_1$-$C_6$-alkyl;
$R^{10}$ $OR^{11}$, $SR^{11}$, $NR^{12}OR^{13}$ or $NHS(O)_2R^{14}$;
$R^{11}$ H, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, $C_1$-$C_6$-alkoxycarbonyl-$C_1$-$C_6$-alkyl, di($C_1$-$C_6$-alkyl)amino, $C_3$-$C_6$-cycloalkyl, $C_3$-$C_6$-cycloalkyl-$C_1$-$C_6$-alkyl or phenyl-$C_1$-$C_4$-alkyl;
$R^{12}$ H, $C_1$-$C_6$-alkyl, $C_2$-$C_6$-alkenyl, $C_3$-$C_6$-alkynyl, $C_1$-$C_6$-haloalkyl or $C_1$-$C_6$-alkoxy-$C_1$-$C_6$-alkyl;
$R^{13}$ H, $C_1$-$C_6$-alkyl, $C_2$-$C_6$-alkenyl or $C_3$-$C_6$-alkynyl
$R^{14}$ $C_1$-$C_6$-alkyl or di($C_1$-$C_6$-alkyl)amino
$Q^1$ O or S;
$Q^2$ O or S;
X $C_1$-$C_6$-alkylene or $C_1$-$C_6$-haloalkylene;
Y O, S, S(O), $S(O)_2$, NH or N($C_1$-$C_6$-alkyl);
$Z^1$ O or S;
$Z^2$ O or S;
or an agriculturally acceptable salt, amide, ester or thioester thereof, provided the compounds of formula (I) have a carboxyl group.

2. The uracilpyridine of formula (I) according to claim 1 wherein $R^1$ is $CH_3$, and $R^2$ is $CF_3$.

3. The uracilpyridine of formula (I) according to claim 1, wherein $R^3$ is H.

4. The uracilpyridine of formula (I) according to claim 1, wherein $R^6$ is $CH_3$ and $R^7$ is H.

5. The uracilpyridine of formula (I) according to claim 1 wherein $R^{10}$ is $OR^{11}$.

6. The uracilpyridine of formula (I) according to claim 1 wherein X is $CH_2$.

7. The uracilpyridine of formula (I) according to claim 1, wherein Y is S.

8. The uracilpyridine of formula (I) according to claim 1, wherein $Q^1$, $Q^2$, $Z^1$ and $Z^2$, are O.

9. A process for the preparation of a uracilpyridine of formula (I), wherein an acid halide of formula (II)

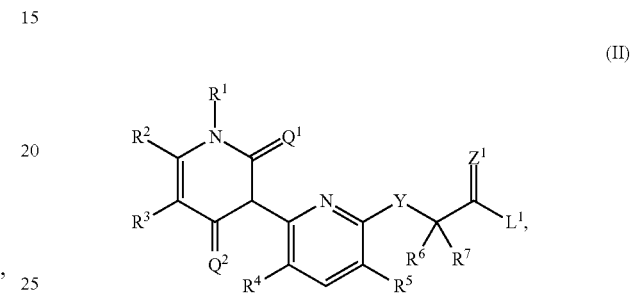

(II)

wherein $R^1$, $R^2$, $R^3$, $R^4$, $R^5$, $R^6$, $R^7$, $Q^1$, $Q^2$, Y and $Z^1$ are as defined in claim 1, and $L^1$ is halogen;
is reacted with a compound of formula (III)

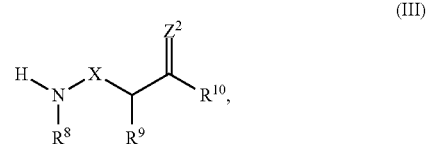

(III)

wherein $R^8$, $R^9$, $R^{10}$, X and $Z^2$,
are as defined in claim 1, in the presence of a base.

10. A formulation comprising an herbicidally active amount of at least one uracilpyridine of formula (I) as claimed in claim 1 and at least one inert liquid and/or solid carrier and, optionally, at least one surface-active substance.

11. A method of controlling undesired vegetation, which comprises allowing an herbicidally active amount of at least one uracilpyridine of formula (I) as claimed in claim 1 to act on plants, their environment or on seed.

* * * * *